United States Patent
Massow et al.

(10) Patent No.: US 9,441,946 B2
(45) Date of Patent: Sep. 13, 2016

(54) IMAGING TECHNIQUE FOR OPTICAL COHERENCE TOMOGRAPHY

(75) Inventors: Ole Massow, Bergen (DE); Henning Wisweh, Supplingenburg (DE); Tobias Jeglorz, Stein (DE)

(73) Assignee: Wavelight GmbH (DE)

( * ) Notice: Subject to any disclaimer, the term of this patent is extended or adjusted under 35 U.S.C. 154(b) by 49 days.

(21) Appl. No.: 14/398,118

(22) PCT Filed: May 3, 2012

(86) PCT No.: PCT/EP2012/001900
§ 371 (c)(1),
(2), (4) Date: Oct. 30, 2014

(87) PCT Pub. No.: WO2013/164004
PCT Pub. Date: Nov. 7, 2013

(65) Prior Publication Data
US 2015/0116661 A1    Apr. 30, 2015

(51) Int. Cl.
| | |
|---|---|
| *A61B 3/14* | (2006.01) |
| *A61B 3/00* | (2006.01) |
| *G01B 9/02* | (2006.01) |
| *A61B 3/10* | (2006.01) |
| *A61B 3/117* | (2006.01) |

(52) U.S. Cl.
CPC .......... *G01B 9/02035* (2013.01); *A61B 3/102* (2013.01); *A61B 3/117* (2013.01); *G01B 9/02091* (2013.01)

(58) Field of Classification Search
USPC .................................................. 351/206, 246
See application file for complete search history.

(56) References Cited

U.S. PATENT DOCUMENTS 6,134,003 A    10/2000   Tearney et al.

FOREIGN PATENT DOCUMENTS

WO    2010009450 A1    1/2010

*Primary Examiner* — Jack Dinh

(57) ABSTRACT

A technique for optical coherence tomography is provided. As to a device aspect of the technique, an imaging device comprises a base defining a rotation axis, a scanning and focusing assembly mounted to the base for rotation about the rotation axis, and a drive unit for rotationally driving the scanning and focusing assembly about the rotation axis. The scanning and focusing assembly includes a focusing device for focusing a beam of imaging radiation to produce a focused beam of imaging radiation having a focus, a scanning member for scanning the beam of imaging radiation, and a controller coupled to the drive unit and the scanning member and configured to control the scanning member to cause movement of the focus along a predetermined trajectory with respect to the scanning and focusing assembly.

13 Claims, 12 Drawing Sheets

IMAGING TECHNIQUE FOR OPTICAL COHERENCE TOMOGRAPHY

CROSS REFERENCE TO RELATED APPLICATIONS

Figure 1:
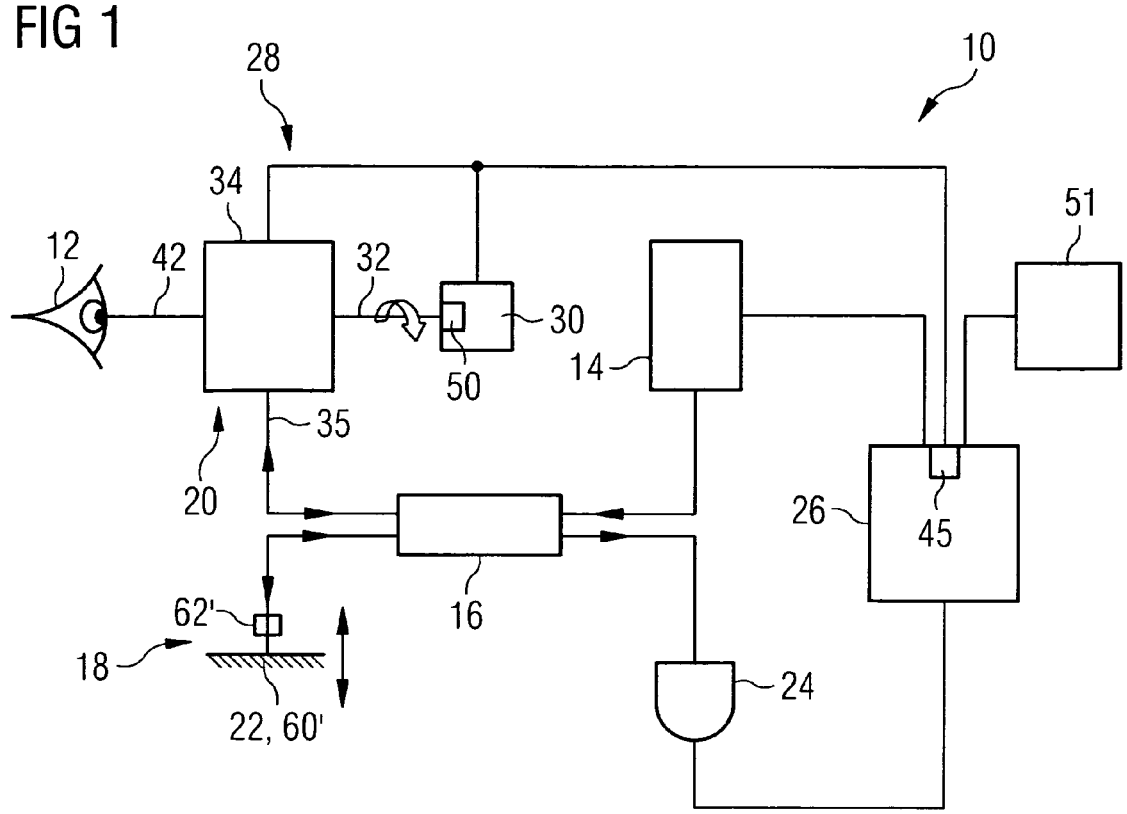

This application is a section 371 national stage phase of International Application No. PCT/EP2012/001900, filed 3 May 2012, titled "IMAGING TECHNIQUE FOR OPTICAL COHERENCE TOMOGRAPHY," which is hereby incorporated by reference in its entirety.

The present disclosure relates to techniques for Optical Coherence Tomography (OCT) imaging.

Optical Coherence Tomography is a non-invasive, and often non-contact, imaging technique. Light with a defined coherence length irradiates a sample. The sample reflects light at different depths of penetration, which encodes information in the phase of the light. The light from the sample is superimposed with coherent light of a reference branch.

For acquisition of two- or three-dimensional OCT images of the sample, scanning and focusing assemblies are employed to scan a focus of a focused beam of imaging radiation along a specific focal scan trajectory. To this end, a scanning member usually varies the angle of incidence at which the beam enters a focusing device. The focusing device focuses the beam to single points of the focal scan trajectory depending on the angle of incidence.

A focal scan trajectory, as used herein, can be understood as a one-dimensional geometric object or as a curved and/or non-curved focal trace line. A trajectory is axial symmetric, if there exists a straight line (the so-called symmetry axis) such that for each point P of the trajectory there exists a point P' of the trajectory, wherein a connecting line [PP'] is divided equally in half by the symmetry axis. If the trajectory is not axial symmetric, it is axial asymmetric or free of axial symmetry.

For example, an axial symmetric focal scan trajectory can be realized by a scanning and focusing assembly having a radially (or rotationally) symmetric focusing device such as a simple lens.

Yadav et al. disclose in *Scanning system design for large scan depth anterior segment optical coherence tomography*, Optics Letters, Vol. 35, No. 11, page 1774 to 1776, a scanning system with a radially asymmetric focusing device for guiding an OCT light beam, wherein in a first range of scan positions of the scanning system the light beam is incident nearly normal to two corneal surfaces and an anterior lens surface, and in a second range of scan positions the light beam is incident nearly normal to a posterior lens surface.

It is an object of embodiments of the present invention to provide an OCT imaging technique that yields three-dimensional imaging of a substantially rotationally symmetric sample such as a human eye.

In an embodiment, an imaging device comprises: a base defining a rotation axis; a scanning and focusing assembly mounted and/or coupled to the base for rotation about the rotation axis; and a drive unit for rotationally driving the scanning and focusing assembly about the rotation axis; wherein the scanning and focusing assembly includes a focusing device for focusing a beam of imaging radiation to produce a focused beam of imaging radiation having a focus, and a scanning member for scanning the beam of imaging radiation; and a controller coupled to the drive unit and the scanning member and configured to control drive unit and/or the scanning member to cause movement of the focus along a predetermined trajectory with respect to the scanning and focusing assembly. The predetermined trajectory, as used herein, can be understood as a focal scan trajectory (short: trajectory).

This embodiment allows for rotation of the scanning and focusing assembly as a whole about the rotation axis of the base. The scanning and focusing assembly may be mounted for rotation with respect to the base by at least 180 degrees and preferentially by substantially 360 degrees. The scanning and focusing assembly may be rotated by any angle between 0° and 180° or 0° and 360°. The rotation of the scanning and focusing assembly results in a spatial rotation of the trajectory with respect to the base as the position and orientation of the trajectory is related to the position and orientation of the scanning and focusing assembly. Therefore, during a complete rotation about e.g. 360°, the trajectory describes a rotationally symmetric focal scan figure. Thus, the present embodiment allows for a rotationally symmetric focal scan figure to be generated using a focal scan trajectory which may be free of axial symmetry.

Moreover, the trajectory may be free of any symmetry at all. The trajectory may have a shape so that a three-dimensional focal scan figure resulting from rotation of the trajectory has separate surfaces which are mutually offset along the rotation axis. In this way, the focal scan figure may be adapted to one or more complex formed structures such as a set of different interfaces of a human eye. In particular, these interfaces may relate to interfaces shifted along the optical axis of the eye, such as a corneal surface and a human lens surface, corresponding to different axial depths of the eye.

As the scanning and focusing assembly is rotatable as a whole, the scanning member may be designed for one-dimensional scanning. In other words: the scanning member may have solely a one-dimensional scanning capability. It does not require a two- or higher-dimensional scanning capability. For example, the scanning member may be a scanning mirror, wherein, in particular, the scanning mirror may have only a single scanning axis, about which the mirror is rotatable. This allows for a cost reduction of the scanning member and an increase of the reliability of the imaging device, since the scanning member is of less complex design. A further advantage of this feature: Commonly used scanning members having a two-dimensional scanning unit comprising two spatially separated scanning mirrors usually cause optical distortion, which has to be corrected. By dispensing a two-dimensional scanning unit, there is no need for such a correction.

As the scanning and focusing assembly can be rotated to an arbitrary rotation angle, the controller and the scanning member may be configured to scan the focus of the focused beam of imaging radiation radially or laterally away from the rotation axis defined by the base. In particular, the trajectory and the rotation axis defined by the base may intersect. Additionally or alternatively, the trajectory and the rotation axis defined by the base may be arranged such that the trajectory describes—during rotation—a focal scan figure, whose geometry fits within the physical dimensions of a human eye. This ensures that the trajectory "remains" inside an eye to be observed during scanning and during rotation of the scanning and focusing assembly.

The controller may be configured to control the drive unit to drive the scanning and focusing assembly into each of a plurality of different rotational positions with respect to the base. The plurality of different rotational positions may be distributed equidistantly or continuously between, e.g. 0° and 180° or 0° and 360°. The controller may be configured to control the scanning member to move the focus along the predetermined trajectory with respect to the scanning and focusing assembly in each different rotational position of the scanning and focusing assembly. The controller may be configured to scan the angle of incidence, under which the beam of radiation enters the focusing device. In particular, the controller may be configured to adjust a first rotational position of the scanning and focusing assembly in a first step, to scan the angle of incidence in a second step, to adjust a second rotational position of the scanning and focusing assembly in a third step and to scan the angle of incidence again in a fourth step. This allows a star-like scanning pattern for tomographic imaging of the sample.

The focusing device may comprise at least one radially asymmetric mirror and/or at least one radially asymmetric lens. A radially asymmetric lens may consist of one half of a first radially symmetric lens with a first focal length cut along its optical axis into two pieces and of one half of a second radially symmetric lens with a second focal length different from the first focal length cut along its optical axis into two pieces. A radially asymmetric mirror may consist of one half of a first radially symmetric focusing mirror with a first focal length cut along its optical axis into two pieces and of one half of a second radially symmetric focusing mirror with a second focal length different from the first focal length cut along its optical axis into two pieces. The radially asymmetric components enable an arbitrary focal scan trajectory.

The trajectory may comprise a plurality of trajectory sections. In particular, the scanning and focusing assembly may have such imaging properties that the focus of the focused beam of imaging radiation is scanned along a discontinuous and/or discontinuously differentiable trajectory. The beam of imaging radiation entering the focusing device under an angle of incidence within a first angle range may exit the focusing device from a first portion of an exit surface and may be focused on a first trajectory section, wherein the beam of imaging radiation entering the focusing device under an angle of incidence within a second angle range may exit the focusing device from a second portion of the exit surface different from the first portion and may be focused on a second trajectory section different from the first trajectory section. This allows for a section-wise adaption of the trajectory to different and locally separated internal structures of the sample.

For at least one of the plurality of trajectory sections a direction of propagation of the focused beam of imaging radiation may be independent of a position of exit of the focused beam of imaging radiation from the focusing device. In other words: Beams of imaging radiation exiting from the first portion of the exit surface may be focused on the first trajectory section such that the directions of propagation of the focused beams are parallel for all angles of incidence within the first angle range. This enables the realization of a telecentric imaging design. A telecentric imaging design can be used, inter alia, to determine the distance between the imaging device and the sample to be observed by the imaging device. This, in turn, avoids the usage of spacers between the imaging device and the sample, such as a contact glass.

Additionally or alternatively, for at least one of the plurality of trajectory sections a beam axis of the focused beam of imaging radiation may be oriented perpendicularly or orthogonally to the trajectory. In other words: Beams of imaging radiation exiting from the first portion of the exit surface may impinge along the direction of propagation of the focused beams on the first trajectory section perpendicularly. Such a perpendicular orientation has the advantage of an increased signal-to-noise ratio of tomographic images of the trajectory section.

For at least one first section of the plurality of trajectory sections a direction of propagation of the focused beam of imaging radiation may be independent of a position of exit of the focused beam of imaging radiation from the focusing device, whereas for at least one second section of the plurality of trajectory sections a beam axis of the focused beam of imaging radiation is oriented perpendicularly or orthogonal to the trajectory. This allows for the realization of a telecentric imaging design for the first trajectory section together with an imaging design for the second trajectory section, in which the orientation of the propagation direction is perpendicular to the second trajectory section. Such an imaging device would benefit from both the above mentioned advantages regarding the use of a telecentric imaging design and a perpendicular imaging design.

All the trajectory sections may be plain/flat. Alternatively, parts of the trajectory sections may be bent/curved, whereas another part of the trajectory sections may be plain/flat. Still alternatively, all the trajectory sections may be bent/curved.

A convergence angle of the focused beam of imaging radiation may be different for different ones of the plurality of trajectory sections. In other words: A convergence angle of beams of imaging radiation exiting the focusing device from the first portion of the exit surface may be different from a convergence angle of the beams of imaging radiation exiting the focusing device from the second portion of the exit surface. The convergence angle for each trajectory section may be adapted such that the corresponding focus has a desired spot size. This enables the realization of different lateral resolutions of images for the different trajectory sections and/or the adaption of the depth of imaging for the different trajectory sections. In the latter case, the axial resolution can be kept the same for all the different trajectory sections, since the axial resolution depends only one the coherence length of the beam of radiation. Alternatively, the convergence angle of the focused beams may also be constant for the plurality of trajectory sections. In this case, also the lateral resolution is kept constant for the plurality of trajectory sections.

A first optical path, as used herein, may be understood as the optical path between the scanning member and a first trajectory section of the focal scan trajectory. A second optical path may be understood as the optical path between the scanning member and a second trajectory section of the focal scan trajectory. In other words: The first and second optical paths of the beam of imaging radiation can be associated with first and second sections of the predetermined trajectory, respectively.

The scanning and focusing assembly may comprise at least one optical path length adjuster for adjusting an optical path length difference between first and second optical paths of the beam of imaging radiation. The optical path length adjuster may be arranged in the first optical path and/or the second optical path. This enables the compensation of optical path length differences. Alternatively or additionally, the optical path length adjuster may be arranged in a reference path of an interferometer. The interferometer may comprise a beam splitter defining the reference path and a sample path and couples light emitted from a light source into the reference path and the sample path and superimposing return light from the reference path and the sample path. The scanning and focusing assembly may be disposed in the sample path. To implement the optical path length adjuster in the interferometer, the reference path may comprise an adjustable reflection mirror such that the optical path length of the reference path is adjustable relative to the optical path length of the sample path. The interferometer may be realized by a free-space setup or by a fiber based setup. Alternatively or additionally to the realization by use of an adjustable reflection mirror, the optical path length adjuster may be realized as a module in the reference arm of the interferometer, the module being adapted to switch between different states, wherein each state corresponds to a different optical path length of the reference path relative to the optical path length of the sample path.

Additionally or alternatively, the scanning and focusing assembly may comprise at least one dispersion adjuster for adjusting a chromatic dispersion of a first optical path of the beam of imaging radiation with respect to a chromatic dispersion of a second optical path of the beam of imaging radiation. The dispersion adjuster may be arranged in the first optical path and/or in the second optical path. This enables the compensation of different chromatic dispersions. Adjusting the chromatic dispersion of an optical path, as used herein, is understood as adjusting the dispersion, to which the beam is subjected during a round-trip propagation on this optical path.

The scanning and focusing assembly may comprise at least one folding mirror arranged in the first optical path and/or in the second optical path. The folding mirror may be arranged in the scanning and focusing assembly such that the first optical path, the second optical path, or both the first optical path and the second optical path are folded. This allows for a compact design of the scanning and focusing assembly.

The imaging device may comprise an optical fiber coupler connectable to an optical fiber of a fiber optic beam splitter. The optical fiber coupler may be configured to guide light exiting the optical fiber to the scanning member. The optical fiber coupler may be configured to collimate light exiting the optical fiber to a collimated beam of imaging radiation.

In another embodiment, the present invention provides an optical coherence tomography apparatus comprising: a source for emitting coherent light; a base defining a rotation axis; a beam splitter defining a reference path and a sample path, the beam splitter coupling the emitted light from the source into the reference path and the sample path and superimposing return light from the reference path and the sample path;
a detector for measuring an intensity of the superimposed light; a scanning and focusing assembly disposed in the sample path and mounted to the base for rotation about the rotation axis, the scanning and focusing assembly including a focusing device for focusing a beam of light to produce a focused beam of light having a focus and a scanning member for scanning the beam of light; a drive unit for rotationally driving the scanning and focusing assembly about the rotation axis; and
a controller coupled to the drive unit and the scanning member and configured to control the scanning member to cause movement of the focus along a predetermined trajectory with respect to the scanning and focusing assembly.

The light can be understood as the imaging radiation, in particular OCT imaging radiation. The beam splitter may be mounted to the base.

A method of imaging a human eye using optical coherence tomography comprises the steps of providing a scanning and focusing assembly which is supported for rotation about a rotation axis; focusing a beam of OCT imaging radiation onto the eye using the scanning and focusing assembly; rotating the scanning and focusing assembly into each of a plurality of different rotational positions; and in each different rotational position of the scanning and focusing assembly, scanning the beam of OCT imaging radiation to thereby move a focus of the beam of OCT imaging radiation along a predetermined trajectory with respect to the scanning and focusing assembly.

The scanning step may consist of scanning the beam of OCT imaging radiation along a linear scan path.

To the extent that a method or individual steps of a method of imaging is/are described in this description, the method or individual steps of the method can be executed by an appropriately configured imaging device and/or OCT apparatus. Analogous remarks apply to the elucidation of the mode of operation of an imaging device and/or OCT apparatus that execute(s) method steps. To this extent, apparatus features and method features of this description are equivalent.

Figure 2:
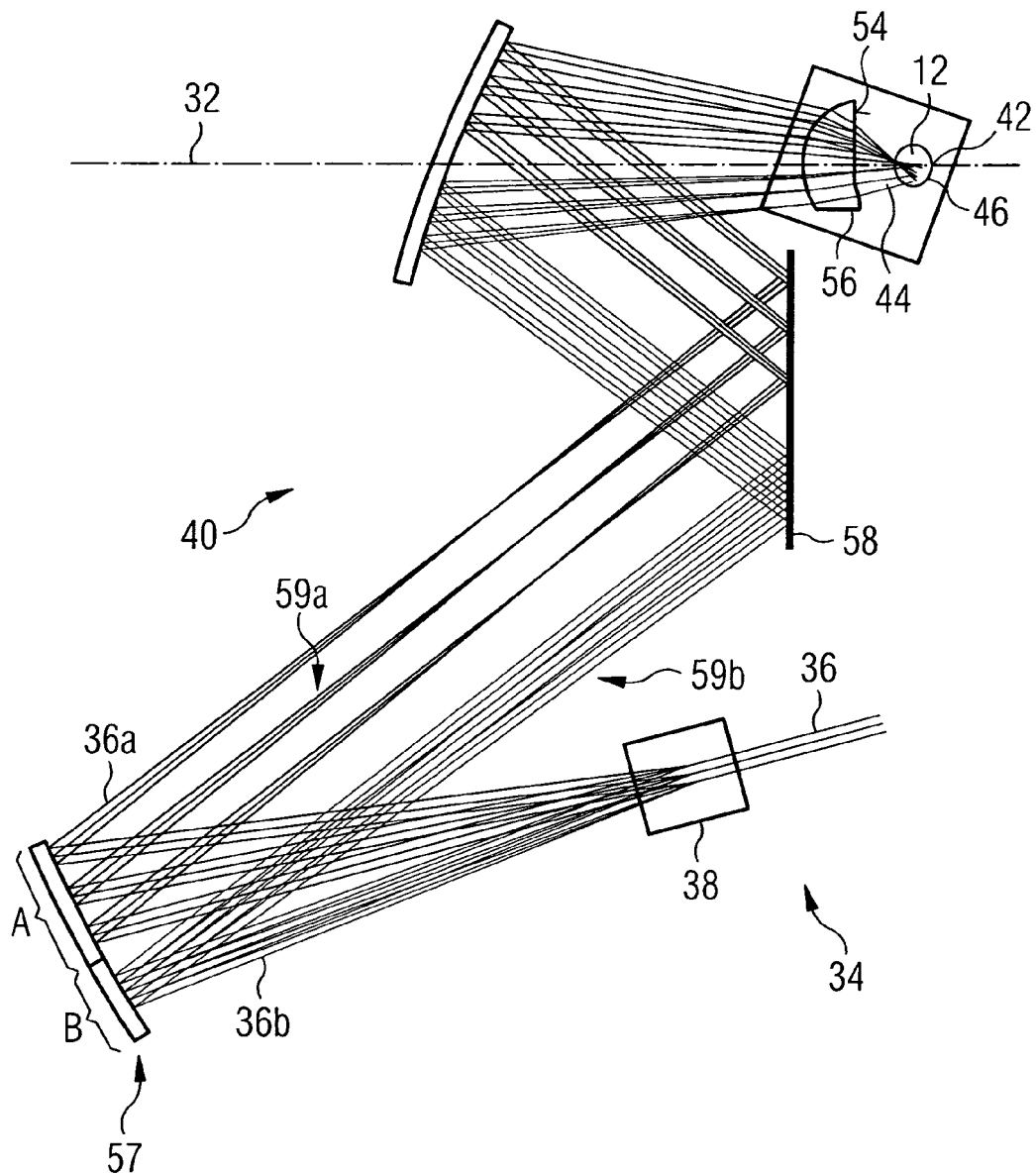
Figure 3:
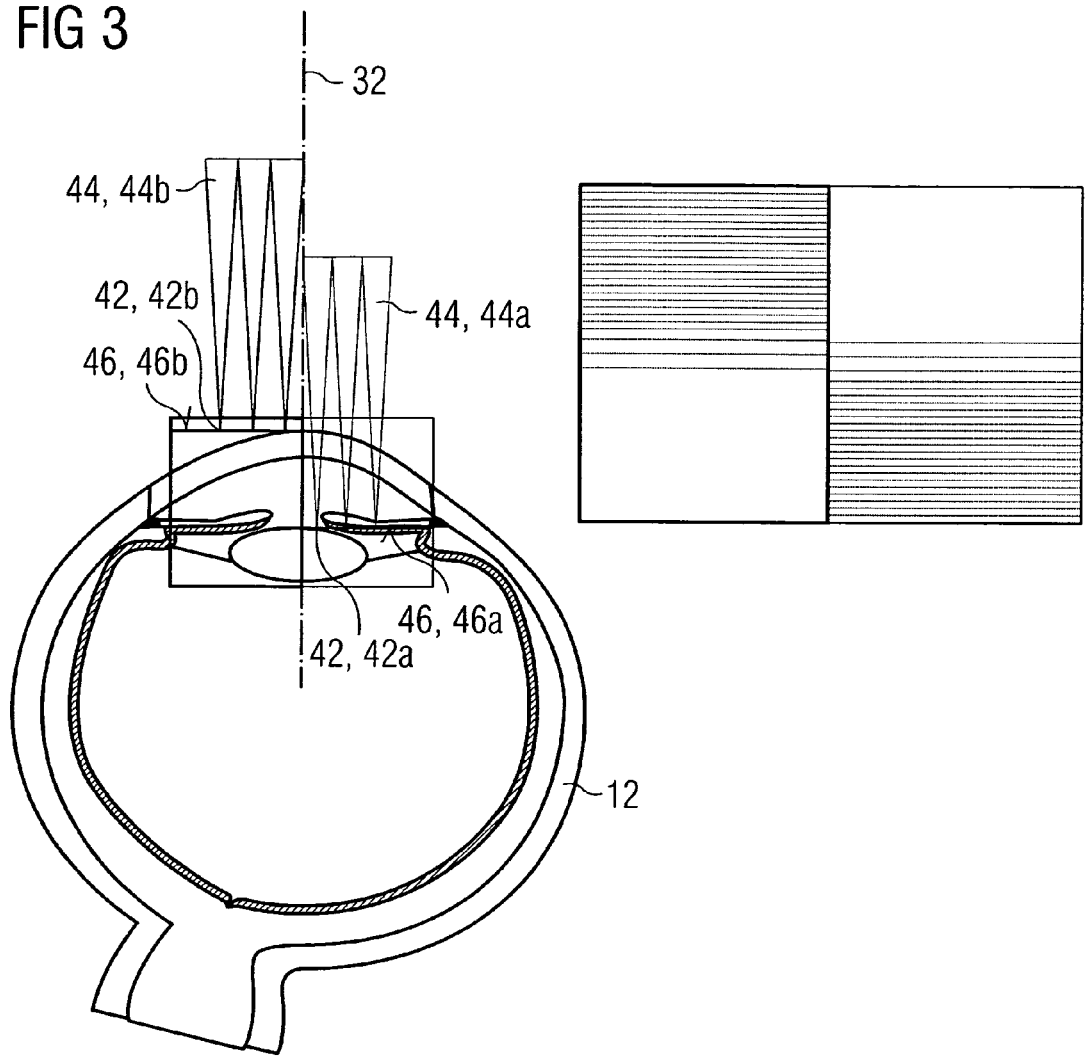
Figure 4:
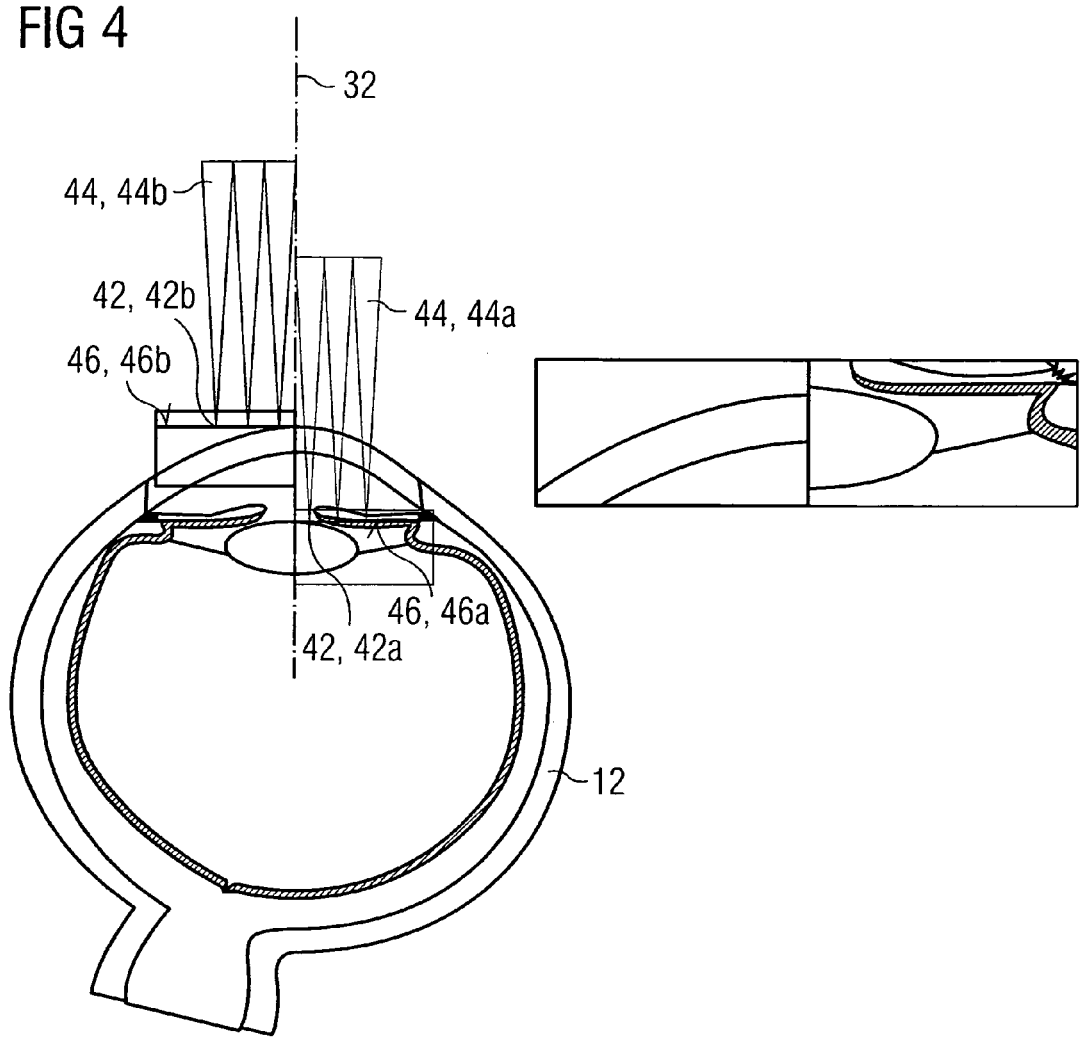
Figure 5:
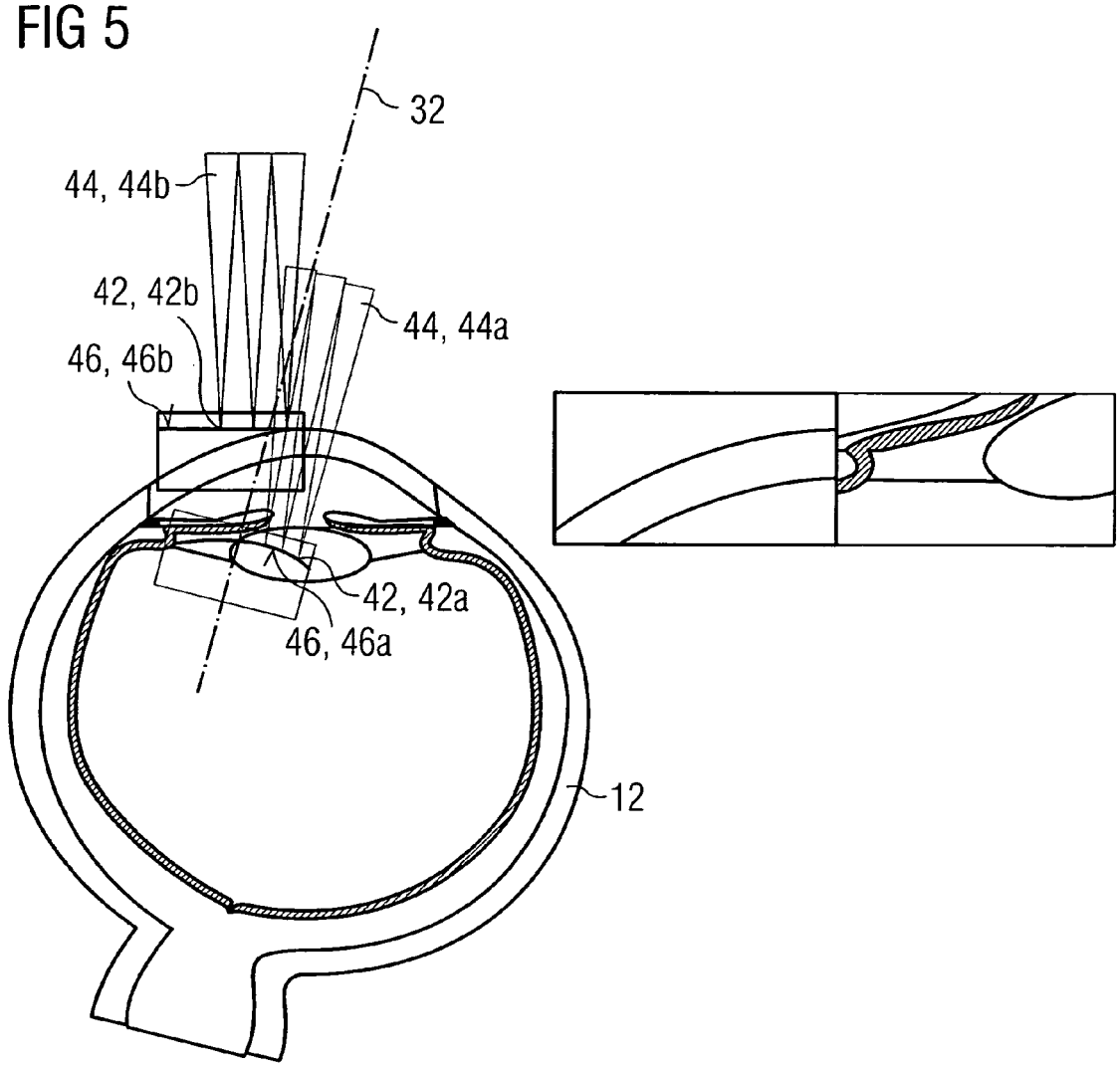
Figure 6:
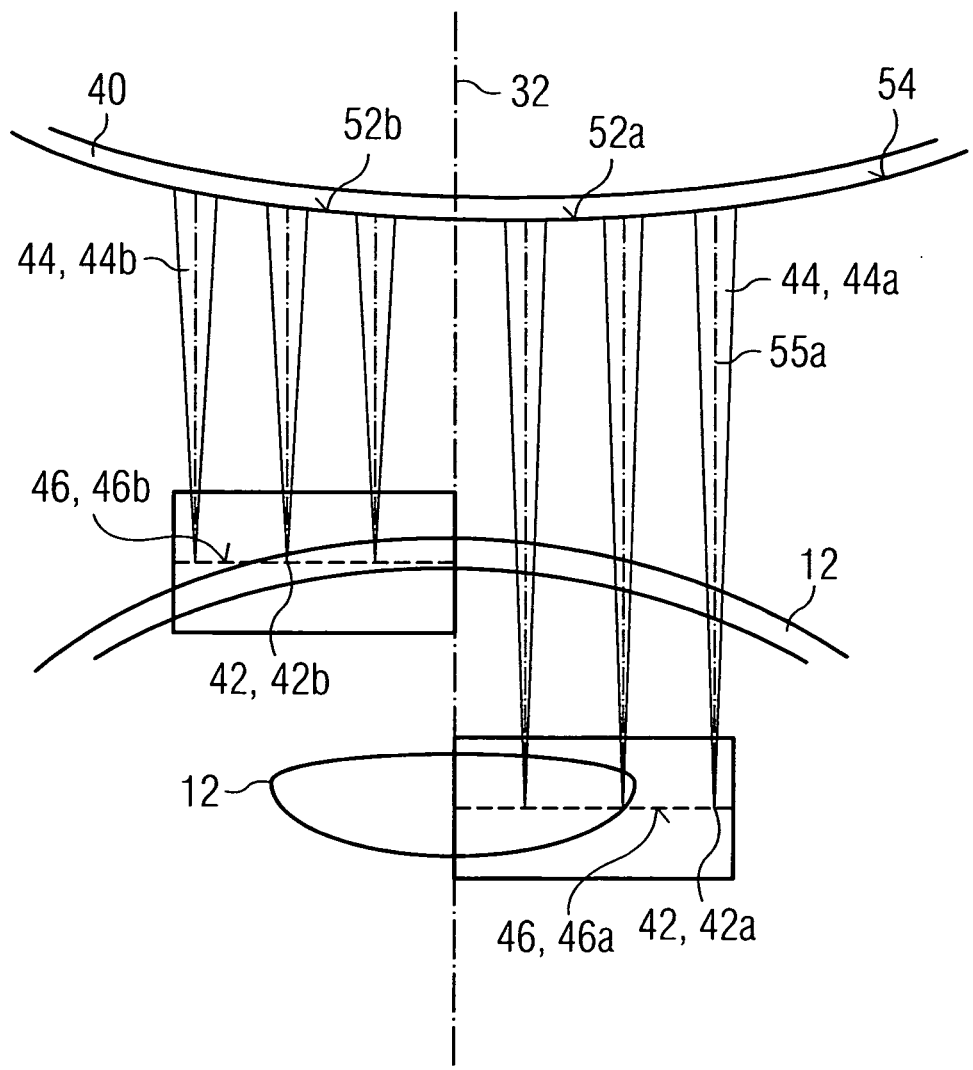
Figure 11:
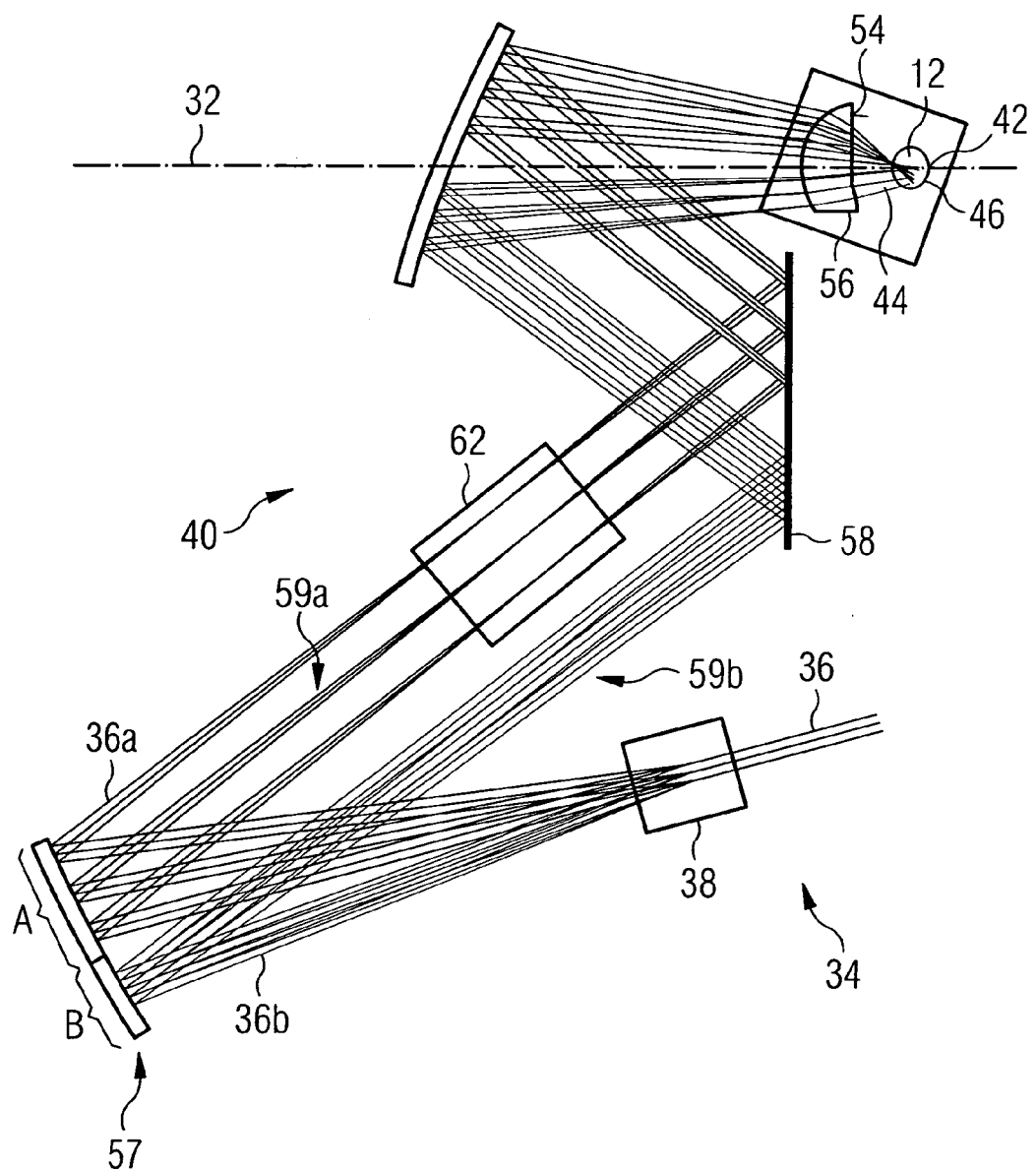
Figure 12:
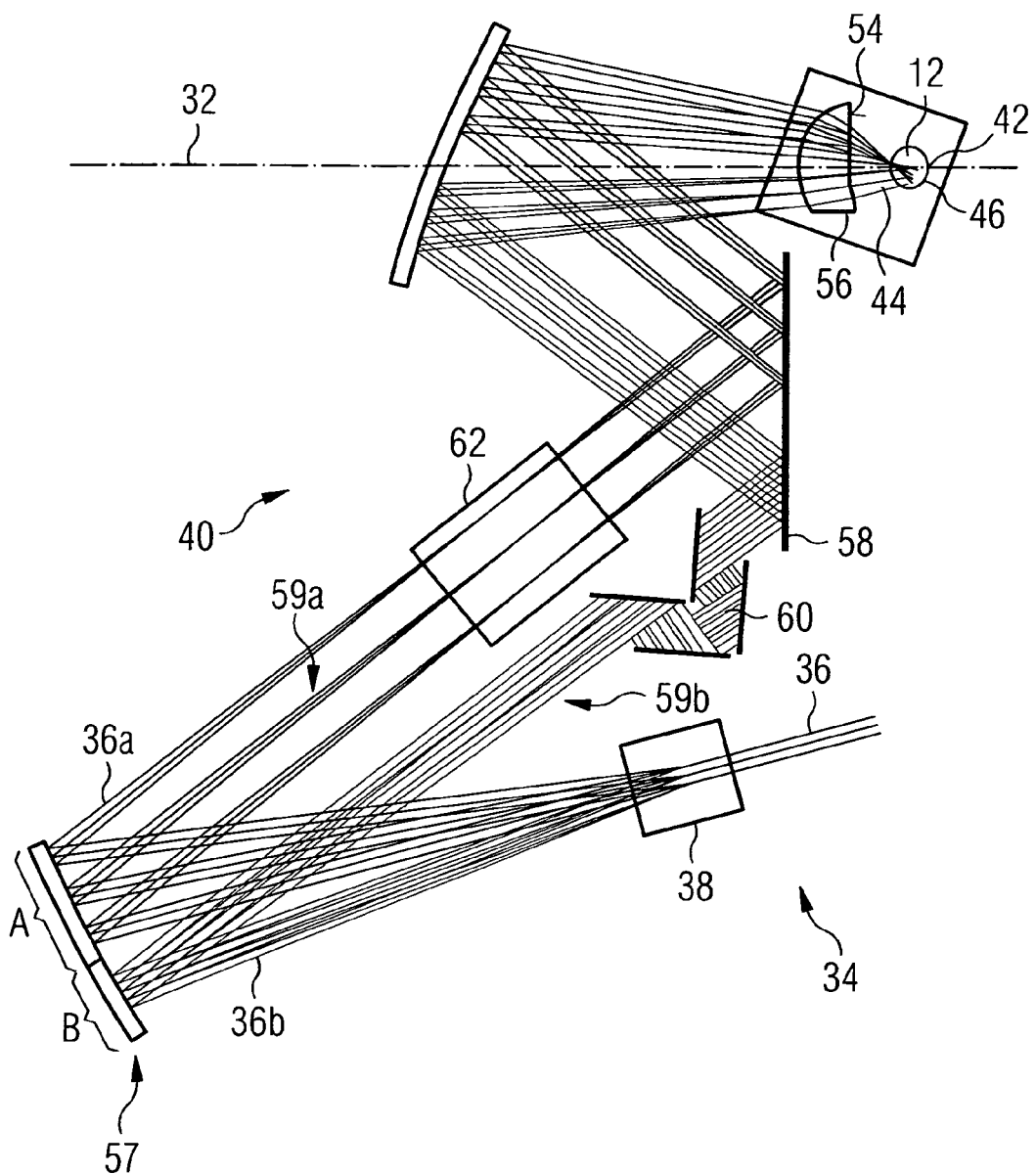

Further features, advantages and technical effects of the invention will become apparent from the following description of exemplary embodiments with reference to the accompanying drawings, in which:

FIG. 1 schematically illustrates an embodiment of an OCT apparatus;

FIG. 2 schematically illustrates a first embodiment of an imaging device;

FIGS. 3 to 10 schematically illustrate different examples for focal scan trajectories of an imaging device;

FIG. 11 schematically illustrates a second embodiment of an imaging device;

FIG. 12 schematically illustrates a third embodiment of an imaging device;

An apparatus 10 for optical coherence tomography (OCT) is shown in FIG. 1. The OCT apparatus serves for creating three-dimensional (3D) tomograms of a sample 12 shown in the exemplary case as a human eye. The optical coherence tomography is based, for example, on time-domain (TD) OCT or on frequency-domain (FD) OCT.

The apparatus 10 comprises a light source 14 for generating coherent light. The source 14 is designed, for example, for the purpose of FD OCT as a tuneable light source or emits a spectrum of coherent light that is broadband within the frequency space. The light emitted from the source 14 is directed onto a beam splitter 16. The beam splitter 16 couples the coherent light from the source 14 into a reference path 18 and into a sample path 20.

The light that has been branched off in the reference path 18 impinges onto a mirror 22, which reflects the light back to the beam splitter 16 collinearly. For the purpose of TD OCT the mirror 22 may be displaceable along the direction of light propagation in the reference path 18 (indicated by the double arrow in FIG. 1). To this end, the adjustable mirror 22 can be regarded as an optical path length adjuster 60'. The light that has been branched off in the sample path 20 impinges onto the sample 12, which back-scatters or reflects back the light in the direction of the beam splitter 16. The beam splitter 16 collinearly superimposes light returning from the reference path 18 and from the sample path 20 so as to form an interference beam, whose intensity of interference is measured by a detector 24. The detector 24 registers the intensity of the interference as a function of the time, the wavelength and/or the wave number. For this purpose the detector 24 may be a photodiode or spectrometer. The detected signal is transferred to a control unit 26, which derives OCT images therefrom. Components 16, 22 and 24 thus realize an interferometer. By a corresponding adaption of these components 16, 22, 24, the interferometer may be realized as a free-space setup or a fiber-based setup.

In the sample path 20, an imaging device 28 is arranged. The imaging device 28 comprises a base 30 defining a rotation axis 32 and a scanning and focusing assembly 34 supported by the base 30 so as to be rotatable with respect to the base 30 about the rotation axis 32 (as shown, for example, by the arrow in FIG. 1). The base 30 is understood as a fixed frame such as a wall or a stand.

Light from the beam splitter 16 is guided by an optical fiber 35 within the sample path 20 and coupled into the imaging device 28 by use of an optical fiber coupler (not shown), which collimates light exiting from the optical fiber 35 to a collimated beam 36 of imaging radiation, which enters the scanning and focusing assembly 34.

Various embodiments of the scanning and focusing assembly 34 are shown in FIGS. 2, 11 and 12. The collimated beam 36 reaches a scanning member 38, which deflects the beam 36 to a focusing device 40 for focusing the beam 36 to produce a focus 42 of a focused beam 44 of imaging radiation.

The scanning and focusing assembly 34 comprises a controller 45 that controls the scanning member 38 to scan the focus 42 of the focused beam 44 along a predetermined focal scan trajectory 46 with respect to the scanning and focusing assembly 34. As an example, the controller 45 of the scanning and focusing assembly 34 can be implemented in the control unit 26 as shown in FIG. 1. However, the controller 45 may also be implemented as a separate component, which is connectable to the control unit 26 of the apparatus 10 for exchanging communication and/or control signals.

Close-up examples of the focal scan trajectory 46 are shown in FIGS. 3 to 10. While in FIGS. 3 to 7 the examined sample 12 is—at least partially—shown, it is omitted in FIGS. 8 to 10 for a clearer illustration.

The scanning and focusing assembly 34 as a whole can be spatially rotated about the rotation axis 32 of the base 30. This rotation results in a spatial rotation of the focal scan trajectory 46 with respect to the base 30 as the position and orientation of the focal scan trajectory 46 is related to the position and orientation of the scanning and focusing assembly 34. Therefore, during a complete rotation about, for example, 360°, the focal scan trajectory 46 describes a rotationally symmetric focal scan figure.

Figure 7:
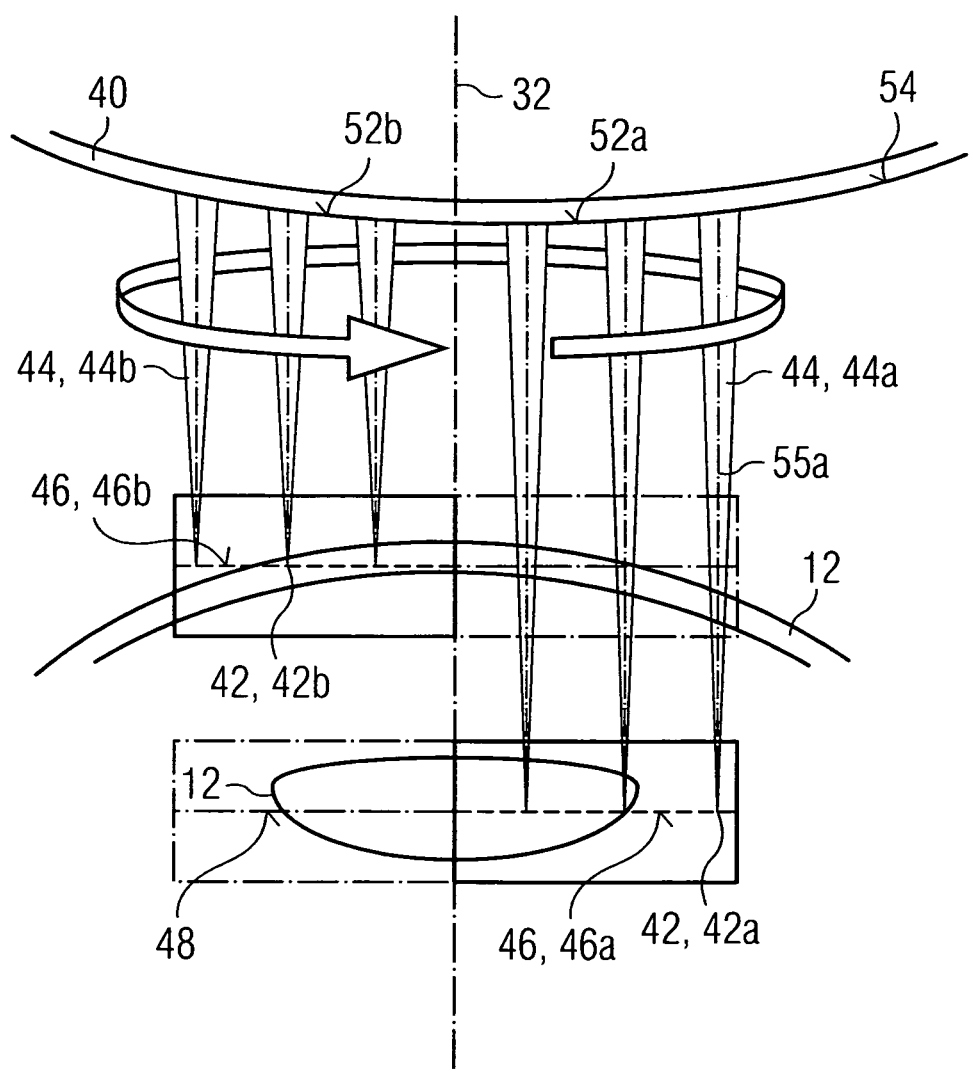
Figure 8:
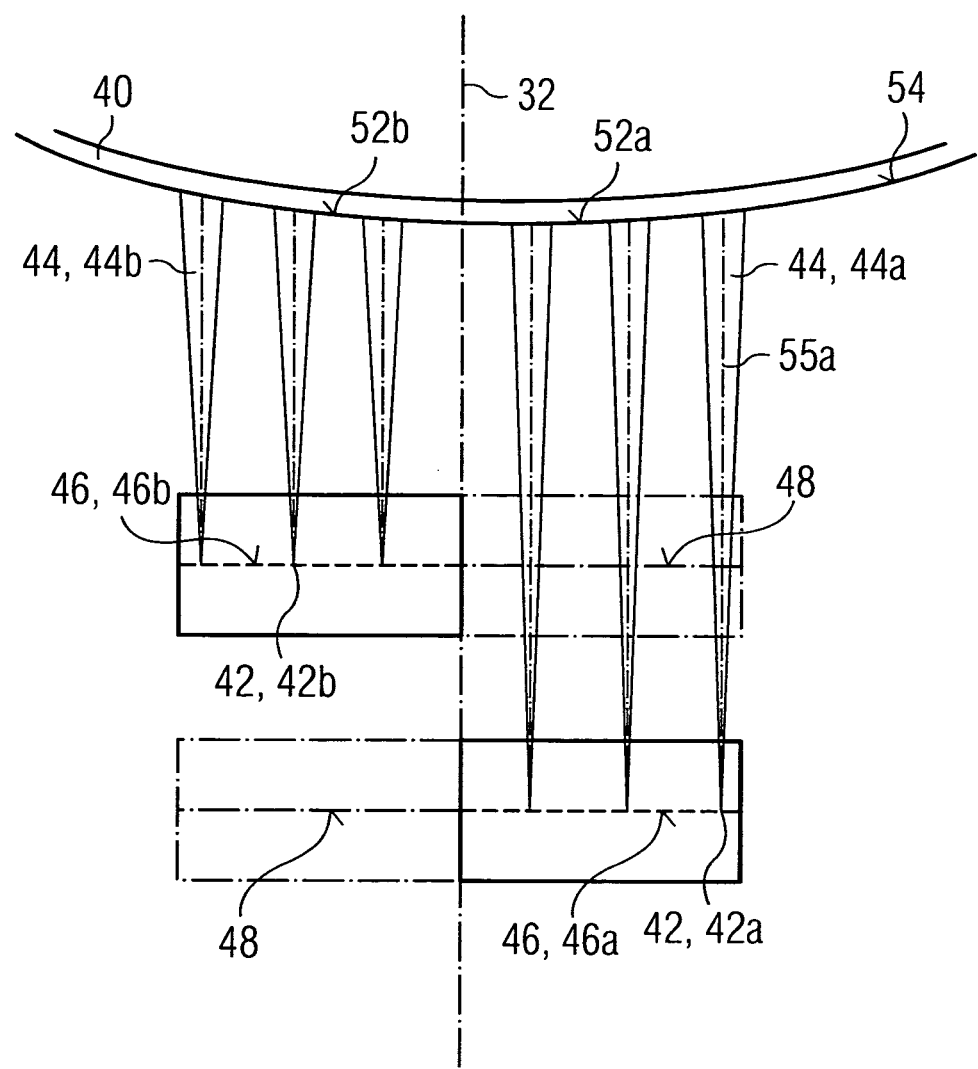
Figure 9:
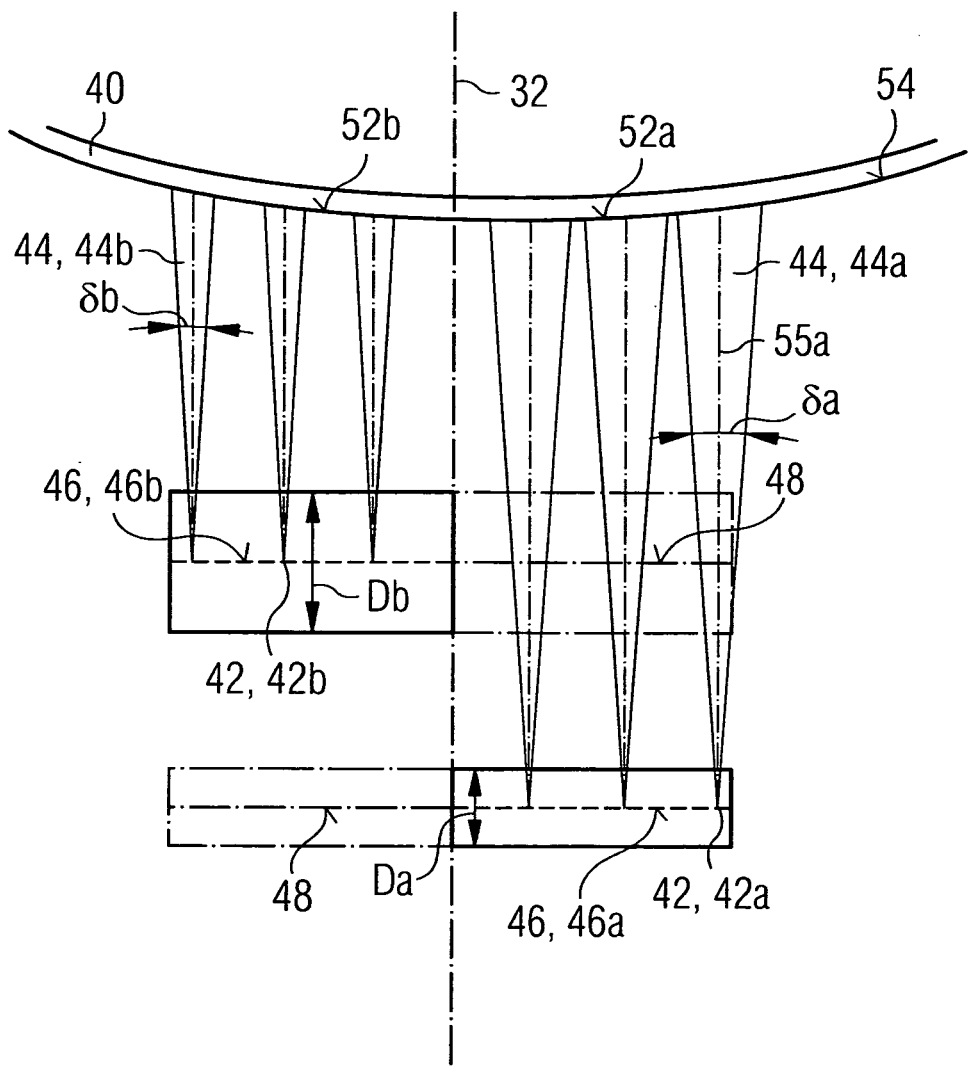
Figure 10:
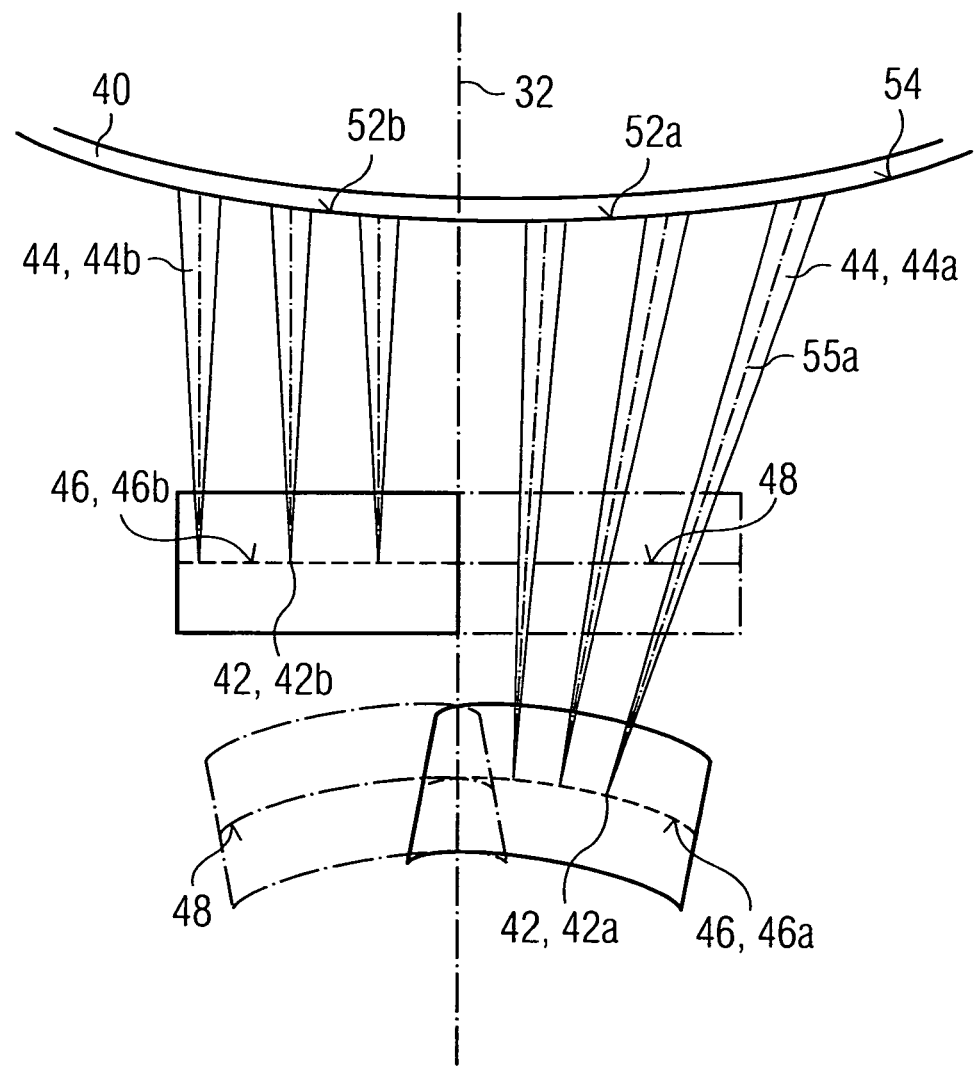

Such a rotation is schematically shown in FIG. 7. In this illustration, the rotation of the focal scan trajectory 46 with respect to the rotation axis 32 is represented by an arrow resulting in a focal scan figure illustrated by the focal scan trajectory 46 and the rotated focal scan trajectory 48. Such focal scan figures are also shown in FIGS. 8 to 10. Embodiments of the invention thus enable a rotationally symmetric focal scan figure to be generated out of a not necessarily axial symmetric focal scan trajectory 46. The rotation symmetry axis of the focal scan figure is the rotation axis 32.

The controller 45 controls a drive unit 50 of the imaging device 28 to rotate the scanning and focusing assembly 34 about the rotation axis 32 to a plurality of different rotational positions of the scanning and focusing assembly 34 with respect to the base 30.

For creating a 3D tomogram of the sample 12, the controller 45 controls the drive unit 50 and the scanning member 38 to scan the focus 42 of the focused beam 44 along the focal scan trajectory 46 in each of the plurality of different rotational positions of the scanning and focusing assembly 34. The signal detected by the detector 24 during this operation is processed by the control unit 26, which then constructs a 3D tomogram of the sample 12 out of the measured signal. The tomogram is displayed on a display 51.

The scanning member 38 must only have a one-dimensional scanning capability, since the scanning and focusing assembly 34 can be rotated to an arbitrary rotation angle. It is sufficient that the focus 42 of the focused beam 44 can be set along a radial direction by the scanning member 38, i.e. a lateral direction with respect to the rotation axis 32. The one-dimensional scanning design allows for a cost reduction of the scanning member 38. Further, the complexity of the scanning member 38 is reduced resulting in a higher reliability of the imaging device 28. A further advantage of this feature: Commonly used scanning members having a two-dimensional scanning unit comprising two spatially separated scanning mirrors usually cause optical distortion, which has to be corrected. By dispensing a two-dimensional scanning unit, there is no need for such a correction.

Another advantage of the rotatability of the scanning and focusing device 34 is that even out of discontinuous and/or discontinuously differentiable focal scan trajectories 46 such as shown in FIGS. 3 to 10 a rotationally symmetric focal scan figure can be obtained by rotating the scanning and focusing device 34.

The examples for focal scan trajectories 46 in FIGS. 3 to 10 comprise two separate trajectory sections 46a and 46b. That is: A beam 36a (see FIG. 2) deflected into the focusing device 40 under an angle of incidence within a first angle range A exits the focusing device 40 from a first portion 52a (see e.g. FIG. 6) of an exit surface 54 and is focused on a first trajectory section 46a. A beam 36b (see FIG. 2) deflected into the focusing device 40 under an angle of incidence within a second angle range B exits the focusing device 40 from a second portion 52b (see e.g. FIG. 6) of the exit surface 54 different from the first portion 52a and is focused on a second trajectory section 46b different from the first trajectory section 46a.

According to the examples shown in FIGS. 6 to 9, for the first trajectory section 46a a direction of propagation (=beam axis) 55a of the focused beam 44a is independent of a position of exit of the focused beam 44a from the focusing device 40. Beams 36a exiting from the first portion 52a are thus focused on the first trajectory section 46a such that the directions of propagation (=beam axes) 55a of the focused beams 46a are parallel for all angels of incidence within the first range A. This represents the realization of a telecentric imaging design.

As shown in FIGS. 6 to 10, for the first trajectory section 46a the beam axis 55a of the focused beam 46a is oriented perpendicularly or orthogonally to the focal scan trajectory 46a. Beams 46a exiting from the first portion 52a along their direction of propagation 55a impinge on the first trajectory section 46a perpendicularly. Such an imaging design has the advantage of an increased signal-to-noise ratio for images of the first trajectory section 46a.

Both trajectory sections 46a, 46b may be plain/flat, see e.g. FIG. 9. Alternatively, one trajectory section 46a may be bent/curved, whereas another trajectory section 46b may be plain/flat, see e.g. FIG. 10. Still alternatively, both trajectory sections 46a, 46b may be bent/curved (not shown).

As shown in FIG. 9, a convergence angle of the focused beam 46 is different for different ones of the plurality of trajectory sections 46a, 46b. The convergence angle δa of beams 44a exiting from the first portion 52a is larger than the convergence angle δb of beams 44b exiting from the second portion 52b. The convergence angles δa, δb for each trajectory section 46a, 46b may thus be adapted such that the respective foci 42a, 42b have different spot sizes. This allows for the realization of different lateral resolutions of images of the different trajectory sections 46a, 46b and/or the adaption of the depth of imaging Da, Db for the different trajectory sections 46a, 46b as indicated in FIG. 9. The axial resolution can be kept the same for all the different trajectory sections 46a, 46b, since the axial resolution depends only one the coherence length of the beam 36 emitted by the identical light source 14.

Alternatively, the convergence angle of the focused beams 44 may also be constant for the plurality of trajectory sections 46a, 46b, see e.g. FIGS. 6, 7, 8 and 10. In this case, also the lateral resolution is kept constant for the plurality of trajectory sections 46a, 46b.

As shown in FIGS. 3 to 7, the different trajectory sections 46a, 46b can be adapted to different contours of sample structures, such as—in the case of an eye—the cornea, the human lens, the iris or the like, or to different interfaces shifted along the optical axis of the eye thus relating to different depths of the eye. This is possible as the focal scan trajectory 46 must not necessarily have any symmetry but can be arbitrary complex and the rotatability feature of the imaging device 28 "restores" rotation symmetry for the focal scan figure.

As shown in the embodiments of FIGS. 2, 11 and 12, the focusing device 40 comprises a radially asymmetric lens 56 and a radially asymmetric mirror 57 to realize the above mentioned designs of the focal scan trajectories 46, 46a, 46b. Additionally, the focusing device 40 comprises a folding mirror 58 arranged in a first optical path 59a and a second optical path 59b. The first optical path 59a runs between the scanning member 38 and the first trajectory section 46a and represents all paths traveled by beams 36a within the first angle range A. The second optical path 59b runs between the scanning member 38 and the second trajectory section 46b and represents all paths traveled by beams 36b within the second angle range B. The folding mirror 58 allows for a compact design of the scanning and focusing assembly 34. That is: The first and the second optical paths 59a, 59b of the beam 36, 44 of imaging radiation are associated with the first and the second trajectory sections 46a, 46b of the focal scan trajectory 46, respectively.

As shown in the embodiment of FIG. 12, the scanning and focusing assembly 34 comprises an optical path length adjuster 60 arranged in the second optical path 59a, which adjusts the optical path length difference between the first optical path 59a and the second optical path 59b. This allows for compensation of optical path length differences. Alternatively or additionally, as already stated above, an optical path length adjuster 60' may also be arranged in the reference path 18, see FIG. 1.

As shown in the embodiments of FIGS. 11 and 12, the scanning and focusing assembly 34 comprises a dispersion adjuster 62 arranged in the first optical path 59a, which adjusts a chromatic dispersion of the first optical path 59a with respect to a chromatic dispersion of the second optical path 59b. This allows for compensation of different chromatic dispersions. Alternatively or additionally, a dispersion adjuster 62' may be arranged in the reference path 18, see FIG. 1.

The invention claimed is:

1. An imaging device comprising:
   a base that defines a rotation axis;
   a scanning and focusing assembly coupled to the base and configured to rotate about the rotation axis; and
   a drive unit configured to rotationally drive the scanning and focusing assembly about the rotation axis;
   the scanning and focusing assembly further comprising:
   a focusing device comprising at least one radially asymmetric mirror or at least one radially asymmetric lens and configured to focus a beam of imaging radiation to produce a focused beam of imaging radiation having a focus;
   a scanning member configured to scan the beam of imaging radiation; and
   a controller coupled to the drive unit and the scanning member and configured to control the scanning member to cause movement of the focus along a predetermined trajectory with respect to the scanning and focusing assembly.

2. The imaging device of claim 1, wherein the controller is configured to:
   control the drive unit to drive the scanning and focusing assembly into each of a plurality of different rotational positions with respect to the base, and
   control the scanning member to move the focus along the predetermined trajectory with respect to the scanning and focusing assembly in each different rotational position of the scanning and focusing assembly.

3. The imaging device of claim 1, wherein the scanning and focusing assembly rotates with respect to the base by at least 180 degrees.

4. The imaging device of claim 1, wherein the predetermined trajectory is free of axial symmetry.

5. The imaging device of claim 1, wherein the scanning and focusing assembly is designed for one-dimensional scanning.

6. The imaging device of claim 1, wherein:
   the predetermined trajectory comprises a plurality of trajectory sections, and
   for at least one trajectory section, a direction of propagation of the focused beam of imaging radiation is independent of a position of exit of the focused beam of imaging radiation from the focusing device.

7. The imaging device of claim 1, wherein:
   the predetermined trajectory comprises a plurality of trajectory sections, and
   for at least one trajectory section, a beam axis of the focused beam of imaging radiation is oriented perpendicularly to the trajectory.

8. The imaging device of claim 1, wherein:
   the predetermined trajectory comprises a plurality of trajectory sections, and
   a convergence angle of the focused beam of imaging radiation is different for different trajectory sections.

9. The imaging device of claim 1, wherein the scanning and focusing assembly comprises:
   an optical path length adjuster configured to adjust an optical path length difference between first and second optical paths of the beam of imaging radiation associated with first and second sections of the predetermined trajectory, respectively.

10. The imaging device of claim 1, wherein the scanning and focusing assembly comprises:
    a dispersion adjuster configured to adjust a chromatic dispersion of a first optical path of the beam of imaging radiation associated with a first section of the predetermined trajectory with respect to a chromatic dispersion of a second optical path of the beam of imaging radiation associated with a second section of the predetermined trajectory.

11. An optical coherence tomography apparatus comprising:
    a source configured to emit coherent light;
    a base that defines a rotation axis;

a beam splitter configured to define a reference path and a sample path, the beam splitter coupling the emitted light from the source into the reference path and the sample path and superimposing return light from the reference path and the sample path;

a detector configured to measure an intensity of the superimposed light;

a scanning and focusing assembly disposed in the sample path and mounted to the base for rotation about the rotation axis, the scanning and focusing assembly comprising:

a focusing device comprising at least one radially asymmetric mirror or at least one radially asymmetric lens and configured to focus a beam of light to produce a focused beam of light having a focus; and a scanning member configured to scan the beam of light;

a drive unit configured to rotationally drive the scanning and focusing assembly about the rotation axis; and a controller coupled to the drive unit and the scanning member and configured to control the scanning member to cause movement of the focus along a predetermined trajectory with respect to the scanning and focusing assembly.

12. A method of imaging a human eye using optical coherence tomography, the method comprising the steps of:

providing a scanning and focusing assembly that is supported for rotation about a rotation axis;

focusing a beam of OCT imaging radiation onto the eye using the scanning and focusing assembly, the scanning and focusing assembly comprising at least one radially asymmetric mirror or at least one radially asymmetric lens;

rotating the scanning and focusing assembly into each of a plurality of different rotational positions; and in each different rotational position of the scanning and focusing assembly, scanning the beam of OCT imaging radiation to thereby move a focus of the beam of OCT imaging radiation along a predetermined trajectory with respect to the scanning and focusing assembly.

13. The method of claim 12, wherein the scanning the beam of OCT imaging radiation comprises scanning the beam of OCT imaging radiation along a linear scan path.

\* \* \* \* \*